US006289115B1

(12) United States Patent
Takeo

(10) Patent No.: US 6,289,115 B1
(45) Date of Patent: Sep. 11, 2001

(54) MEDICAL NETWORK SYSTEM

(75) Inventor: Hideya Takeo, Kanagawa-ken (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/249,093

(22) Filed: Feb. 12, 1999

(30) Foreign Application Priority Data

Feb. 20, 1998 (JP) .................................................. 10-037873

(51) Int. Cl.[7] .................................................. G06T 1/20
(52) U.S. Cl. .................... 382/130; 345/501; 709/200; 600/437; 128/920; 128/922; 378/98.2; 378/98.5
(58) Field of Search .................................... 345/501, 502, 345/530; 709/200, 217–219; 382/128, 130; 600/407, 437; 128/920, 922; 378/98, 98.2, 98.5

(56) References Cited

U.S. PATENT DOCUMENTS

| | | | | |
|---|---|---|---|---|
| 5,374,965 | * | 12/1994 | Kanno ................................. | 348/705 |
| 5,553,157 | * | 9/1996 | Bourguignon et al. .............. | 382/131 |
| 5,978,562 | * | 11/1999 | Sako ..................................... | 395/115 |
| 6,047,081 | * | 4/2000 | Groezinger et al. ................. | 382/128 |
| 6,084,939 | * | 7/2000 | Tamura ................................ | 378/98.2 |
| 6,101,407 | * | 8/2000 | Groezinger .......................... | 600/407 |
| 6,159,150 | * | 12/2000 | Yale et al. ........................... | 600/437 |
| 6,198,283 | * | 3/2001 | Foo et al. ............................ | 324/309 |
| 6,210,327 | * | 4/2001 | Brackett et al. ..................... | 600/437 |

\* cited by examiner

Primary Examiner—Kee M. Tung
(74) Attorney, Agent, or Firm—Sughrue, Mion, Zinn, Macpeak & Seas, PLLC

(57) ABSTRACT

A medical network system comprising a multitude of reference terminals for referring to diagnosis images can be constructed at low cost and the reference terminals can carry out fast display equivalent to that by a high performance workstation for diagnosis. An image server is loaded with a web server, separately from a server (DICOM server) for providing image data based on a protocol specific to a medical system, so that a web connection to the image server becomes possible. An image processing server loaded with an image processing component for carrying out image processing for display is provided, separately from the image server. The reference terminals obtain image data and a display program from the image server via the web connection, cause the image processing server to execute image processing on the obtained image data, and carry out display alone of the processed image.

6 Claims, 2 Drawing Sheets

MEDICAL NETWORK SYSTEM

BACKGROUND OF THE INVENTION

1. Field of the Invention

The present invention is related to a medical network system wherein various kinds of medical equipment are connected to a network.

2. Description of the Related Art

Images for diagnosis have been exchanged as digital data between doctors and staff for clinical examination or radiology, through a network connecting imaging modalities such as a CT apparatus, a laser printer for outputting images, a server computer for storing and managing the images (hereinafter called an image server), and a diagnosis terminal, in order to improve efficiency in hospital operations.

Recently, in order to connect medical equipment of different manufacturers to each other, standardization of a network protocol dedicated for a medical system has been in progress. For example, the DICOM (Digital Imaging and Communications in Medicine) standard generated by the ACR-NEMA committee (ACR: American College of Radiology, NEMA: National Electrical Manufacturers Association) is a standard for realizing an object-oriented medical network system, and defines the content of various kinds of diagnosis information such as CT image information, clinical examination information, and patient information and the data structure thereof, as well as a procedure for exchanging such diagnosis information as a message (a procedure for requesting services such as storage, acquisition, and printing of images or inquiry about images).

Even when an imaging modality, a printer, a workstation for diagnosis and the like are made by different manufacturers, in a network environment wherein all such devices have DICOM interfaces installed therein (hereinafter called a DICOM network), an application program installed in each device communicates by using the DICOM interfaces. In this manner, exchange of diagnosis information can be realized between the devices.

In the DICOM standard, data formats for information which is not indispensable in a medical system, such as patient information or clinical examination information, are defined in detail, and interfaces for requesting processing upon inquiry of various kinds of information are also defined. Therefore, the development overhead of an application program under the DICOM environment is lighter than under an environment other than the one for DICOM.

For this reason, system construction according to the DICOM standard is generally regarded as desirable for a medical network system.

However, although DICOM network aims at an open environment which is not dependent on manufacturers, it assumes that each device has a DICOM interface. Therefore, in the case where a personal computer assigned to each doctor as a terminal for referring to images is connected to a network in addition to main devices such as imaging modalities, not only the main devices but also all of the personal computers need to have the DICOM interfaces.

Furthermore, since the load of image transfer, image processing, and display processing based on the DICOM standard is heavy, problems such as slow display often occur when a low price personal computer is used as a reference terminal. In order to increase the display speed, a workstation or a personal computer with a higher performance than a conventional one can be used as a reference terminal. However, since at least tens, or hundreds in a large system, of reference terminals are needed, this idea is not preferable in terms of cost.

SUMMARY OF THE INVENTION

Based on considerations of the above problems, an object of the present invention is to realize a low-cost medical network system wherein even a reference terminal can perform fast image processing and fast display equivalent to those obtained with a high performance diagnosis workstation.

A first medical network system of the present invention comprises:

image storing means for storing image data recorded by an image recording modality and an image processing parameter used in image processing of the image data;

first image providing means for providing, based on a medical protocol, the image data stored by the image storing means to an image handling apparatus comprising a communication function based on the medical protocol;

second image providing means for providing, based on a general purpose protocol, the image data and the image processing parameter stored by the image storing means and a predetermined image display program to an image reference terminal comprising a communication function based on the general purpose protocol; and image processing means for carrying out image processing on the image data transferred together with the image processing parameter from the image reference terminal, in response to a request by the image display program executed on the image reference terminal, and for returning the image data having been processed to the image reference terminal; whereby the image reference terminal causes the image processing means to carry out only image processing on the image data provided thereto from the second image providing means, and carries out display processing of the processed image data returned from the image processing means.

The "image recording modality" herein referred to means an apparatus for CT, MRI, or CR, for example. Not only an apparatus (or a system) for acquiring image data by photographing a subject but also an apparatus for acquiring image data by reading a recording medium such as a film are assumed to be included in the image recording modality.

The "image processing parameter" means a parameter such that image data appropriate for diagnosis can be obtained by image processing using the parameter. Upon recording image data or when the image represented by the image data is used for diagnosis for the first time for example, various of image processing is generally carried out thereon so that the image data is made appropriate for diagnosis. More specifically, frequency processing such as sharpness enhancement, enlargement processing on a main portion of the image, or processing for blackening a portion other than an irradiation target is carried out for example. Upon this processing, some systems store the processed image data. However, the system of the present invention stores the image processing parameter separately from the original image data so that no inconvenience will occur upon necessity of the original image data. When the image data are displayed, image processing is carried out on the original image data by using the image processing parameter having been stored.

The term "protocol" widely means all rules regarding data formats and communication procedures. However, in this specification, the term is used to include data formats or communication procedures alone which are standard in the medical industry, and eliminates those originally defined by a manufacturer or by a system constructor.

In other words, the "medical protocol" in this specification means a protocol defined as a standard in the field of medicine, such as the DICOM standard described in the above. Therefore, the "image handing apparatus which comprises a communication function based on the medical protocol" specifically means a DICOM diagnosis workstation, DICOM laser printer, and the like. However, the medical protocol related to the present invention is not limited by DICOM, and includes any medical protocols which may be newly defined through efforts for standardization in the field of medicine.

On the other hand, the "general purpose protocol" does not include any definitions limited for a specific field (for example, patient information or a data format of clinical examination information). In other words, the general purpose protocol means a protocol usable in any industries including the field of medicine.

For example, following the recent spread of the Internet, many general purpose computers, such as Windows personal computers, have a function pre-installed for connecting to the Internet, as a portion of operating systems thereof or as basic software of another kind. Even when this function is not pre-installed, acquisition and installation of a program for realizing such a function have become very easy. The "communication function based on a general purpose protocol" in this specification means such a function related to the Internet.

As a technique in the background of the Internet-related functions for Windows personal computers, ActiveX proposed by Microsoft Corp. has been known. According to this technique, a web server transfers a program (ActiveX control) for carrying out predetermined processing to a terminal requesting the processing, and causes the terminal to execute the processing. In other words, a web browser dealing with ActiveX automatically downloads necessary ActiveX control from a web server and executes the program, in response to an operation by a user on sa screen of the browser.

Therefore, if the "second image providing means" is installed as a web server and ActiveX control for carrying out image processing on image data and displaying the data is provided, a standard Windows personal computer without any special application program installed (except for a browser) can be used as a reference terminal.

Furthermore, as a basic technique which backs ActiveX, a technique called COM (Component Object Model) or DCOM (Distributed COM) exists. According to these techniques, a program executed on one computer can easily call a program (component) on another computer. In other words, processing can be carried out by using a resource (such as a CPU and a memory) of another computer to obtain a result alone.

Therefore, the "image processing means" in the above means a component which carries out predetermined image processing on given image data by using a given image processing parameter, and a computer loaded with such a component. However, since the image processing means carries out image processing for a reference terminal, it is preferable for the computer loaded with the component to be a workstation or a personal computer having higher performance than the reference terminal.

ActiveX and COM are mainly adopted by Windows personal computers. However, the "general purpose protocol" in the present invention is not limited to the Internet-related functions of Windows, but includes any similar network-related techniques, such as the ones developed on UNIX, for example.

Furthermore, a second medical network system of the present invention comprises:

image storing means for storing image data recorded by an image recording modality and an image processing parameter used in image processing of the image data;

first image providing means for providing, based on a medical protocol, the image data stored by the image storing means to an image handling apparatus comprising a communication function based on the medical protocol;

second image providing means for providing the image data and the image processing parameter stored by the image storing means to image processing means, in response to a request by an image reference terminal comprising a communication function based on a general purpose protocol; and the image processing means for carrying out image processing on the provided image data by using the image processing parameter provided together with the image data and for transferring the image data having been processed to the image reference terminal; whereby the image reference terminal causes the image processing means to carry out image processing on the image data provided from the second image providing means, and carries out display processing alone of the processed image data transferred from the image processing means.

In other words, in the first medical network system, its second image providing means transfers image data to its image processing means via its image reference terminal, while the second medical network system transfers image data from its second image providing means to its image processing means directly.

As a function to provide stored image data to various kinds of image handling apparatuses using the image data, the first and the second medical network systems of the present invention comprise not only a server function to provide image data based on a medical protocol such as the DICOM standard, but also a general server function (for example, a web server function) to provide image data based on a general purpose protocol.

In this manner, images can be referred to by using a communication function alone pre-installed in a personal computer (or easily installed therein at low cost). Therefore, a general purpose personal computer can be used as the reference terminal in the medical network systems of the present invention.

By using the network system of the present invention, system construction cost can be reduced, and convenience of the system is improved as well. For example, on a business trip involving a presentation at a meeting of an academic society, images can be obtained from the system by a personal computer comprising standard functions, in the case where the images need to be distributed as references for the presentation.

In the above medical network systems, a server dedicated to image processing alone is provided, and a reference terminal can cause the processing server to carry out image processing. Therefore, the reference terminal has to carry out only the display of the processed image data, and fast display equivalent to that carried out by a high performance personal computer or a workstation is realized even when a low-priced personal computer (without high performance) is used as a reference terminal.

DESCRIPTION OF THE PREFERRED EMBODIMENT

Figure 1:
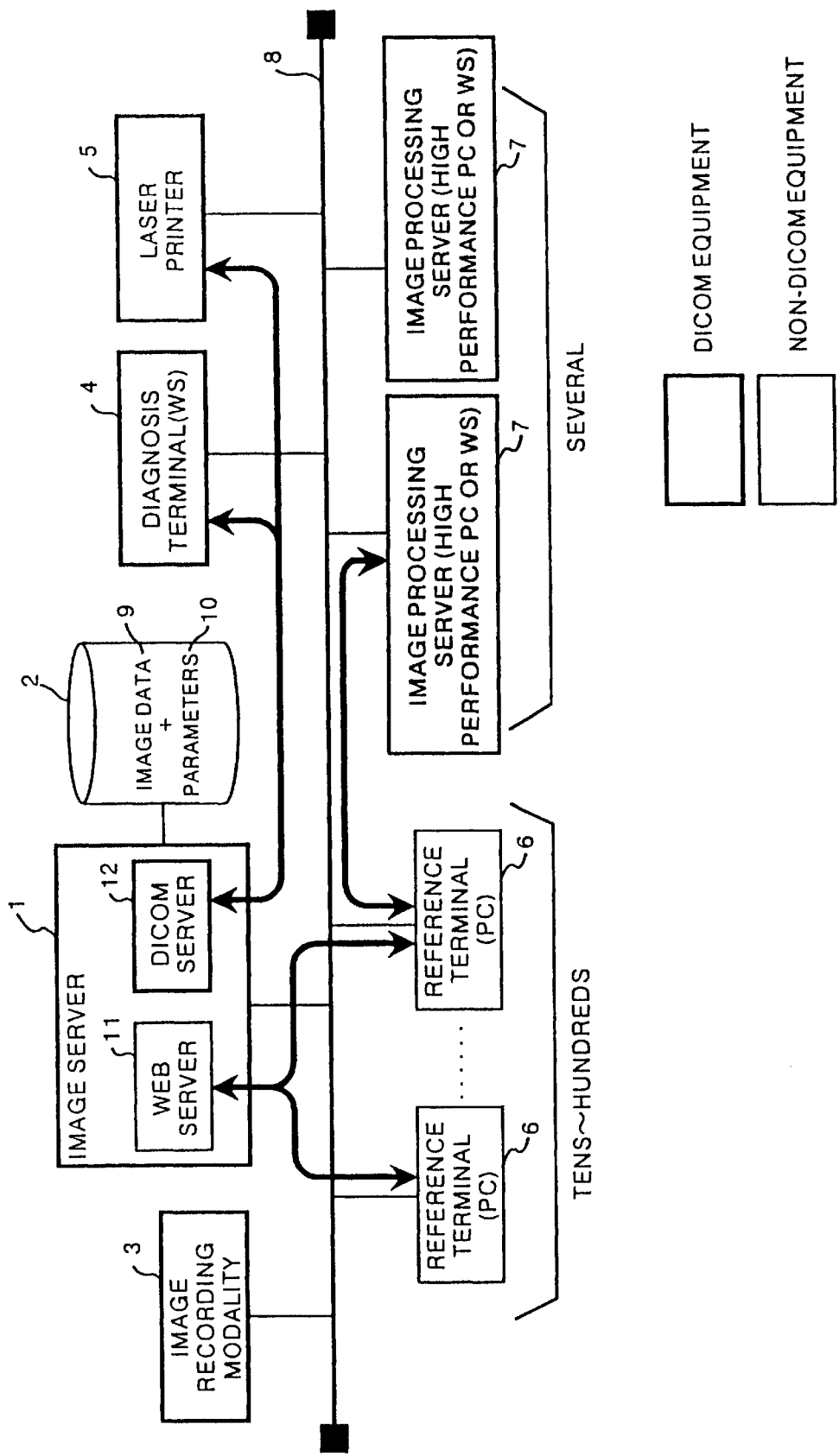
FIG. 1 is a diagram showing an outline of a medical network system of the present invention.

Hereinafter, an embodiment of a medical network system of the present invention will be explained with reference to the accompanying drawings. FIG. 1 shows an outline of the medical network system of the present invention.

In the system shown in FIG. 1, a network 8 is a Local Area Network (LAN), such as Ethernet of FDDI, installed in a hospital. In this case, the LAN is connected to the Internet or another LAN in another hospital via a dedicated line or a public telecommunication line such as ISDN. An image recording modality 3, an image server 1, a diagnosis terminal 4, a laser printer 5, tens or hundreds of reference terminals 6, and several image processing servers 7 are connected to the network 8, as medical equipment composing the medical network system.

The image recording modality 3 is an apparatus or a system for recording an image related to a patient as digital data, such as a CT, MRI, RI, or US apparatus. The image recording modality 3 may record a digital image signal converted from an analogue image signal acquired by photographing. Alternatively, the image recording modality may acquire digital data by reading an image recorded on a film or the like by photographing. In this embodiment, the image recording modality 3 is a DICOM device, and requests storage of an image recorded thereby of the image server 1 which is also a DICOM device.

The image server 3 is a server computer loaded with a DICOM interface and stores image data 9 recorded by the image recording modality 3 in an image database 2. In this case, the image server 1 carries out image processing such as sharpness enhancement on the image data 9 before storing the image data. Various kinds of parameters 10 related to the image processing are also stored in the image database 2, together with the image data 9.

The image server 1 comprises functions to search the image database 2 for image data requested by the diagnosis terminal 4 or by one of the reference terminals 6, to read out the image data and to provide the image data to the terminal. More specifically, the image server 1 is loaded with two application programs, namely a DICOM server 12 for providing image data to the apparatus which has requested the image data according to a procedure defined by DICOM, and a web server 11 for enabling the apparatus connected through the Web to refer to image data.

The DICOM server 12 is a program generated by use of the DICOM interface. The DICOM server realizes various functions. For example, the DICOM server stores an image recorded by the image recording modality 3 in the image database 2, upon request by the image recording modality 3, transfers to the diagnosis terminal 4 the image data 9 and the image processing parameter 10 in response to a request by the diagnosis terminal 4, and outputs the processed image data to the laser printer 5. When a change in an image processing condition has been instructed by the diagnosis terminal 4, the DICOM server 12 stores the image processing parameter 10 after the change again in the image database 2.

Meanwhile, the web server 11 does not use any DICOM interfaces. The web server is a program generated by using a communication function alone pre-installed in an operating system. The web server 11 provides image data for reference to one of the reference terminals 6 connected through the Web.

The diagnosis terminal 4 is a workstation or the like loaded with a diagnosis application program and a DICOM interface for example. The diagnosis terminal is a terminal used by a doctor in a radiological ward or the like, for referring to the image data, for carrying out image processing thereon by changing the image processing parameter upon necessity so that the image becomes appropriate for diagnosis, and for diagnosing with reference to the processed image.

The laser printer 5 outputs processed image data as a visible image. Output of an image to the laser printer 5 is carried out by an instruction given from the diagnosis terminal 4 to the DICOM server 12.

The reference terminals 6 are installed only for referring to image data. In other words, the reference terminals 6 do not carry out processing such as changing an image processing condition or rewriting information in the image database 2. In a conventional medical network system, the reference terminals 6 need to be loaded with DICOM interfaces and a dedicated application program using the DICOM interfaces. In the system of the present invention, the reference terminals 6 do not need to deal with the DICOM standard and no special application programs installed therein are needed either.

The image processing servers 7 are non-DICOM personal computers, and have higher performance than the reference terminals 6. The image processing servers may be workstations. Since one reference terminal is assigned to one doctor for example, a multitude of reference terminals are necessary. However, only several image processing servers 7 are necessary, since they are installed for providing image processing service upon requests by reference terminals 6.

Figure 2:
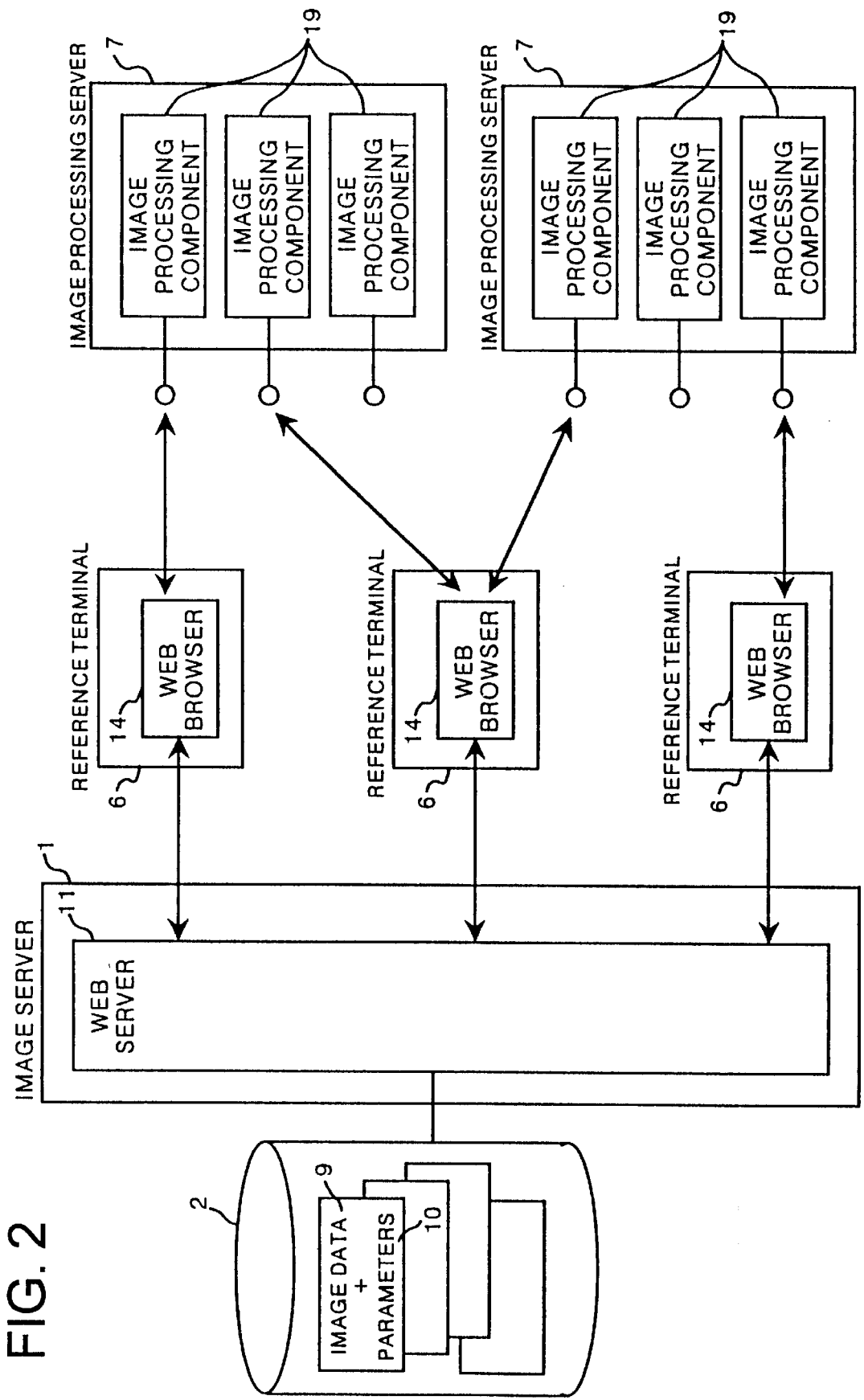
FIG. 2 is a diagram explaining image reference processing by a reference terminal.

FIG. 2 explains a role of the image processing servers 7 and image reference processing by the reference terminals 6. As has been described in the above, in this embodiment, the image server 1 comprises the web server 11, and the web server 11 provides image data 9 and the image processing parameter 10 both stored in the image database 2 to the apparatuses connected through the Web. The reference terminals 6 can connect to the image server 1 through the Web by a function of a web browser 14 such as Internet Explorer or Netscape Navigator.

When display of the image data 9 is requested by one of the reference terminals 6, the image server 1 transfers to the reference terminal 6 ActiveX control for image display processing, the image data 9, and the image processing parameter 10. The web browser 14 carries out the image processing on the transferred image data 9 and displays the data, by running ActiveX control.

In this case, an image processing component 19 for carrying out the image processing has been installed in each of the image processing servers 7. By a request by the web browser 14 for image processing, the image data 9 and the image processing parameter 10 are automatically transferred from the reference terminal 6 requesting the processing to the image processing server 7 which carries out the processing. Image data having been processed are returned from the image processing server 7 to the reference terminal 6 and written in a hard disc of the reference terminal 6. The web browser 14 displays the returned processed image data on a screen. In other words, the reference terminal 6 can carry out the image processing on the image data it refers to, by using a CPU of the image processing server 7.

The image processing server 7 may be loaded with plural kinds of image processing components 19. In this case, the components are automatically selected by the function of ActiveX or COM. Likewise, in the case where one of the image processing servers, if a plurality of the image processing servers exist on the network, is selected, the reference terminals 6 do not need a special function for the selection.

In the form shown in FIG. 2, the image data 9 and the image processing parameter 10 are transferred from the image server 1 to one of the reference terminals 6 and then from the reference terminal 6 to one of the image processing servers 7. However, a form wherein the image data 9 and the like are directly transferred from the image server 1 to the image processing server 7 is also possible.

In this case, when image display is requested by the web browser 14 of one of the reference terminals 6 from the web server 11 of the image server 1, the web server 11 transfers the image data 9 and the image processing parameter 10 to one of the image processing servers 7 which is idle (in the state where image processing service can be provided immediately).

The image processing server 7 having received the image data 9 and the image processing parameter 10 carries out image processing on the image data 9 by using the image processing parameter 10. The image processing server 7 then notifies the web server 11 of processing completion. On this occasion, the file name of the processed image data is also notified to the web server 11. The web server 11 changes a predetermined flag indicating image processing completion from OFF to ON, in response to the notice from the image processing server 7.

While the web server 11 and the image processing server 7 are exchanging information as described in the above, the web browser 14 monitors the flag and detects the image processing completion while staying in connection with the web server 11.

When the web browser 14 detects the image processing completion, the web browser requests from the web server 11 information indicating the image processing server 7 which has carried out the image processing and the file name of the processed image data. Based on the information transferred from the web server 11, the web browser 14 obtains the processed image data from the image processing server 7. The reference terminal 6 can carry out image processing on image data to be referred to thereby by using the CPU of the image processing server 7, and only the display of the processed image data is carried out by the reference terminal 6.

The monitoring of the flag by the reference terminal 6 is possible by a function of a usual web connection, and for data transfer between the reference terminal 6 and the image processing server 7, a standard file transport protocol such as ftp can be used. In other words, the reference terminals 6 do not need any special functions.

In addition to an image server for storing and managing diagnosis images, a medical information managing server such as a His/Ris server which manages hospital information is generally connected to a medical network system. Therefore, the reference terminals 6 may be used as terminals for accessing such servers other than the image server.

In this case, when each server is loaded with a server program for communication according to a protocol which is different between the servers, it has been necessary for the reference terminals in a conventional DICOM network to be loaded with client programs each of which corresponds to each server protocols. However, as in the present invention, when the reference terminals are connected with servers via the Web, the reference terminals only needed browsers and cost per reference terminal can be reduced.

What is claimed is:

1. A medical network system comprising:

image storing means for storing image data recorded by an image recording modality and an image processing parameter used in image processing of the image data;

first image providing means for providing, based on a medical protocol, the image data stored by the image storing means to an image handling apparatus comprising a communication function based on the medical protocol;

second image providing means for providing, based on a general purpose protocol, the image data and the image processing parameter stored by the image storing means and a predetermined image display program to an image reference terminal comprising a communication function based on the general purpose protocol; and image processing means for carrying out image processing on the image data transferred together with the image processing parameter from the image reference terminal, in response to a request by the image display program executed on the image reference terminal, and for returning the image data having been processed to the image reference terminal; whereby the image reference terminal causes the image processing means to carry out image processing on the image data provided thereto from the second image providing means, and carries out display processing of the processed image data returned from the image processing means.

2. A medical network system as claimed in claim 1, wherein the second image providing means is installed as a web server.

3. A medical network system as claimed in claim 1 or 2, wherein the medical protocol is a protocol defined by DICOM.

4. A medical network system comprising:

image storing means for storing image data recorded by an image recording modality and an image processing parameter used in image processing of the image data;

first image providing means for providing, based on a medical protocol, the image data stored by the image storing means to an image handling apparatus comprising a communication function based on the medical protocol;

second image providing means for providing the image data and the image processing parameter stored by the image storing means to image processing means, in response to a request by an image reference terminal comprising a communication function based on a general purpose protocol; and the image processing means for carrying out image processing on the provided image data by using the image processing parameter provided together with the image data and for transferring the image data having been processed to the image reference terminal; whereby the image reference terminal causes the image processing means to carry out image processing on the image data provided from the second image providing means, and carries out display processing of the processed image data transferred from the image processing means.

5. A medical network system as claimed in claim 4, wherein the second image providing means is installed as a web server.

6. A medical network system as claimed in claim 4 or 5, wherein the medical protocol is a protocol defined by DICOM.

* * * * *